(12) United States Patent
Matsuura

(10) Patent No.: US 6,261,988 B1
(45) Date of Patent: Jul. 17, 2001

(54) METAL ION-EXCHANGED PHOSPHORUS-VANADIUM COMPOUND AND SOLID ACID CATALYST USING THE COMPOUND

(75) Inventor: Ikuya Matsuura, Hiroshima-ken (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 0 days.

(21) Appl. No.: 09/261,939

(22) Filed: Mar. 3, 1999

Related U.S. Application Data

(63) Continuation-in-part of application No. 08/812,604, filed on Mar. 6, 1997, now abandoned.

(30) Foreign Application Priority Data

| Mar. 8, 1996 | (JP) | 8-52001 |
| Mar. 8, 1996 | (JP) | 8-52002 |
| Sep. 9, 1996 | (JP) | 8-238209 |
| Mar. 7, 1997 | (MY) | PI-9700953 |
| Mar. 7, 1997 | (SG) | 9700686-0 |
| Mar. 7, 1997 | (TH) | 036105 |
| Mar. 8, 1997 | (CN) | 97104973 |
| Mar. 8, 1997 | (EP) | 97103907 |
| Mar. 8, 1997 | (KR) | 97-7829 |
| Mar. 8, 1997 | (TW) | 86102840 |
| Mar. 10, 1997 | (ID) | P-970746 |

(51) Int. Cl.$^7$ .................... B01J 27/198; C01B 25/26
(52) U.S. Cl. .................................. 502/209; 423/306
(58) Field of Search ................... 502/209; 423/306

(56) References Cited

PUBLICATIONS

"The Role of Fe and Co Dopants During the Activation of the VO(HPO$_4$)·0.5H$_2$O Precursor of the Vanagium Phosphorus Catalyst as Studied by in Situ Laser Raman Spectroscopy," Abdelouahab, F. Ben; Olier, R.; Ziyad, M.; Volta, J.C.,*J. Catal.*, 157(2), 687–97 (English), 1995 (No month).*

"Evidence for a Hydrogen Insertion Compound of Novel Palladium Incorporated Vanadyl Hydrogen Phosphates," Datta, Arunabha; Kelkar, Ravindra Y., *Chem, Commun.* (Cambridge)(1), 89–91 (English), 1996 (No month).*

* cited by examiner

Primary Examiner—Wayne Langel
(74) *Attorney, Agent, or Firm*—Selitto, Behr & Kim

(57) ABSTRACT

A metal ion-exchanged phosphorus-vanadium compound having an interlayer distance in the range of 7.0 to 8.2 Å and an ion exchange ratio of the divalent metal at least 20% obtained by treating vanadyl hydrogen orthophosphate hydrate represented by the formula (1)

VOHPO$_4$ .$n$H$_2$O (1)

wherein n fulfills the expression, 0<n≦2.0, with an aqueous divalent metal salt solution thereby effecting the exchange of N$^+$ present between the layers of said vanadyl hydrogen orthophosphate hydrate, drying the resultant ion exchanged compound, and if necessary calcining the dried ion exchanged compound, a solid acid and a partial oxidation catalyst for hydrocarbons containing the compound.

23 Claims, 8 Drawing Sheets

VOHPO$_4$ • 0.5H$_2$O

○ V   • P   ○ O   ⊛ OH   ⊙ H$_2$O   ● M$^{2+}$

FIG. 1
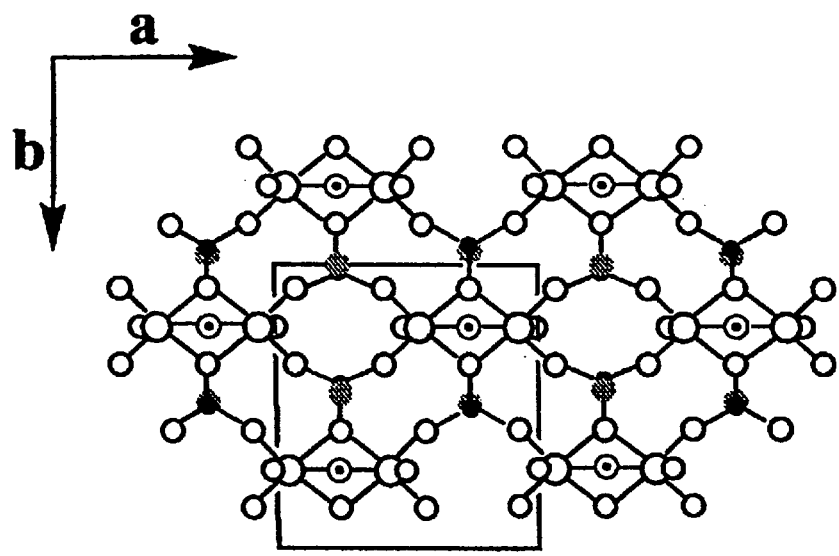
VOHPO₄ · 0.5H₂O
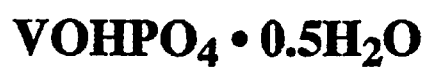
FIG. 2
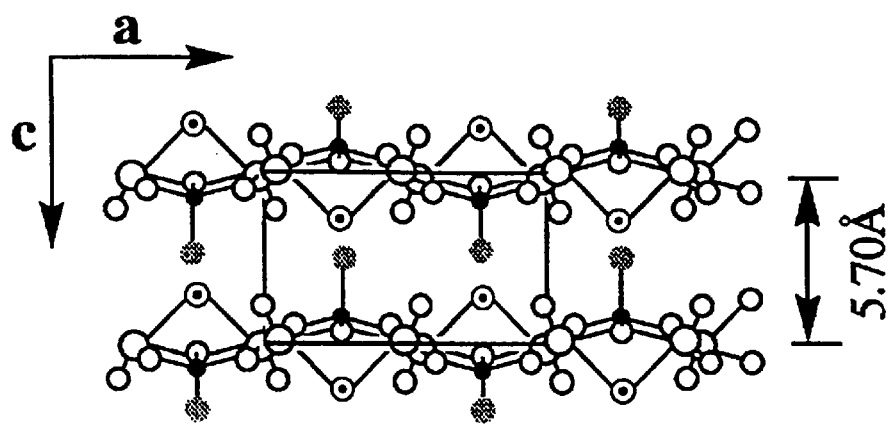
VOHPO₄ · 0.5H₂O
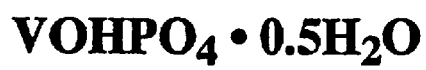

METAL ION-EXCHANGED PHOSPHORUS-VANADIUM COMPOUND AND SOLID ACID CATALYST USING THE COMPOUND

This application is a continuation-in-part of application Ser. No. 08/812,604, filed on Mar. 6, 1997 now abandoned.

BACKGROUND OF THE INVENTION

1. Field of the Invention

This invention relates to a novel metal ion-exchanged phosphorus-vanadium oxide and to a solid acid catalyst which contains this phosphorus-vanadium oxide. More particularly, this novel phosphorus-vanadium oxide is a compound which exhibits a specific d value (lattice spacing, Å). This compound manifests the qualities of a solid acid and, owing to the acid qualities, can be used as a catalyst.

2. Description of the Prior Art

Various studies have been heretofore made concerning the phosphorus-vanadium oxides and physical properties and uses of these oxides have been simultaneously explored for the sake of development. The phosphorus-vanadium compounds are specific in such qualities as the state of oxidation and the configuration and consequently have various crystal structures and find various applications owing to these structures. It is well known that the catalytically effective component of phosphorus-vanadium oxides is divanadyl pyrophosphate, a crystalline oxide which has the composition of $(VO)_2P_2O_7$. This divanadyl pyrophosphate is obtained by synthesizing its precursor, vanadyl hydrogen orthophosphate hydrate ($VOHPO_4.nH_2O$), and thermally dehydrating this precursor. It is also known that the vanadyl hydrogen orthophosphate hydrate as the precursor is an interlayer compound which is formed by the hydrogen bondage of opposed $VOHPO_4$ layers through the medium of water molecules intervening therebetween.

It is widely known that phosphorus-vanadium compounds generally form an effective catalyst for gas-phase oxidation of such hydrocarbons as butane, butene, and butadiene which have four carbon atoms (hereinafter referred to briefly as "C4 hydrocarbons"). Various patterns of X-ray diffraction peaks for identifying these phosphorus-vanadium oxides have been published (JP-A-53-61,588, JP-A-56-41,816, JP-A-56-45,815, JP-A-59-132,938, and JP-A-05-15,781). Various inventions concerning the addition of third components to the phosphorus-vanadium oxides have been also disclosed (JP-A-52-135,580, JP-A-54-30,114, and JP-A-57-111,219).

Reports on phosphorus-vanadium oxides are published in various articles of literature besides the patent publications mentioned above. B. K. Hodnett. ed., Catalysts Today, Vol. 1, No. 5 (1987), for example, carries a detail report.

Datta et al Chem. commun, (1996) pages 89–91 disclose palladium added phosphorus-vanadium compounds prepared by two methods.

The compound prepared form an organic solvent solution shows the same XRD pattern as that of the original vanadyl hydrogen orthophosphate ($VOHPO_4$ .$0.5H_2O$) even if palladium is added, so palladium is not incorporated into the structure thereof, then it is a state of a mixture.

There is possibility that the compound prepared by another method using an aqueous medium is similar compound to a compound wherein a proton between interlayers disclosed in the present invention is exchanged with a divalent metal ion as being clear from XRD pattern of FIG. 6. Especially, about the peak of 7.04 Å in the XRD pattern of FIG. 6, it is thought that there is possibility overlaps with the metal ion-exchanged compound in accordance with the present invention. Then preparation of a palladium added compound was carried out by a method of Datta et al, and comparison between the compound obtained by the method of the present invention and the compound obtained by the method of Datta et al.

Thus, a compound having the XRD pattern of FIG. 1–2a cannot be prepared by the method of Datta et al. About vanadyl hydrogen orthophosphate ($VOHPO_4.0.5H_2O$) which is a precursor, similar compounds can be obtained by both methods using an aqueous mediumoranorganic medium. However, about the palladium added compound, a similar compound shown in FIG. 1–2a cannot be obtained. Further, when Pd ion was measured, but it can almost be detected, so Pd is not exchanged with the proton between interlayers.

Then we have compared the method between the present invention and Datta et al to obtain the difference thereof. In the method of Datta et al, the experiments were carried out using vanadyl hydrogen orthophosphate ($VOHPO_4.0.5H_2O$) in both organic medium and aqueous medium, while in the present invention, the experiments were carried out by ion-exchange method using vanadyl hydrogen orthophosphate ($VOHPO_4.1.5H_2O$) having different crystal water such vanadyl hydrogen orthophosphate having different crystal water have different structures. Such fact is clear from the XRD pattern charts. The XRD patterns of the vanadyl hydrogen orthophosphate of the present invention and those of Datta et al are shown in FIGS. 6 to 9.

FIGS. 6 and 7 are XRD patterns of vanadyl hydrogen orthophosphate ($VOHPO_4.1.5H_2O$) of the present invention. The vanadyl hydrogen orthophosphate having the XRD pattern shown in FIGS. 6 and 7 can easily be ion-exchanged with a divalent metal ion.

FIG. 8 is a XRD pattern of vanadyl hydrogen orthophosphate ($VOHPO_4.0.55H20$) prepared by an organic medium in Datta et al and corresponds to FIG. 1-1 in Datta et al. FIG. 9 is a XRD pattern of vanadyl hydrogen orthophosphate ($VOHPO_4$ $0.5H_2O$) prepared by an aqueous medium in Datta et al and corresponds to FIG. 1-2 in Datta et al.

Abdelouahab et al, Journal of Catalysis 157, 687–697 (1995) discloses a catalyst wherein $VO(HPO_4)0.5H_2O$ precursor of the vanadium phosphorus compound is doped with Fe and Co, but there are no descriptions what portion of the chemical structure of the phosphorus-vanadium compound is exchanged with Fe and Co. Therefore, it is unknown whether it is complexed oxide or mixture.

That is, we have noticed that the $H^{30}$ present between the layers of vanadyl hydrogen orthophosphate hydrate, $VOHPO_4.nH_2O$ and by exchanging the $H^{30}$ with a divalent metal ion, novel metal ion-exchanged phosphorus-vanadium compounds in the present application can be obtained. The resultant compound has an interlayer distance in the range of 7.0 to 8.2 Å, each of which is supported by the XRD (X-ray diffraction analysis) measuring results shown in Tables 1 and 2 in the present application. In particular, hkl=001 and the distance of C axis correspond to the interlayer distance.

In the Tables, the interlayer distance of ordinary vanadyl hydrogen orthophosphate hydrate, $VOHPO_4.0.5H_2O$ is 5.7 Å and the interlayer distance of $VOHPO_4.1.5H_2O$, the interlayer distance has been widen so as to be exchanged with a divalent ion, is 7.97 Å(hkl=001, C axis). By ion exchanging $VOHPO_4.1.5H_2O$ with an ion, a new compound is obtained, the interlayer distance of which is 7.9 Å for Ni, 7.84 Å for Co, 7.31 Å for Cu and 7.25 Å for Zn, respectively.

However, Abdelouahab et al discloses only ordinary vanadyl hydrogen orthophosphate hydrate, $VOHPO_4 \cdot 0.5H_2O$. In according to the measuring results, on the catalyst being doped with Fe and Co, by XRD, it is clearly described that the doped catalyst has the same structure as that of ordinary vanadyl hydrogen orthophosphate hydrate, $VOHPO_4 \cdot 0.5H_2O$. (page 689, right column, line 43 onwards, in particular "only characteristic line of $VOHPO_4 \cdot 0.5H_2O$ are observed.") In addition to the above, FIG. 2 shows that the face (001) is 5.7 Å (2θ=15.50°)

Consequently, the compounds of Abdelouahab et al are said to be mixtures of phosphorous-vanadium compound, Fe and Co or compounds in which Fe and Co are uniformly doped, so that the compounds of Abdelouahab et al are different from those of the present application.

No attempt has ever been made to synthesize a compound having a divalent metal cation exchanged for the $H^{3O}$ ion which intervenes between the opposed layers of the vanadyl hydrogen orthophosphate hydrate, a precursor of a phosphorus-vanadium oxide.

It is well known that the phosphorus-vanadium compound having such a plane structure as illustrated in the form of a model in FIG. 1, e.g. a vanadyl hydrogen orthophosphate hydrate, $VOHPO_4$, is a layer compound which results from the hydrogen bondage through the medium of constitution water intervening between the $VOHPO_4$, layers as shown in FIG. 2. The interlayer distance is generally 5.70 Å. Absolutely no case of having this interlayer proton exchanged with other metal cation has been known to date.

An object of this invention, therefore, is to provide a novel phosphorus-vanadium compound.

Another object of this invention is to provide a novel phosphorus-vanadium compound which is obtained by the exchange of a proton present between opposed layers in the layer structure of a phosphorus-vanadium compound with a metal ion and a method for the production thereof.

Yet another object of this invention is to provide a novel solid acid catalyst.

A further object of this invention is to provide a catalyst appropriate for gas-phase partial oxidation of a hydrocarbon.

SUMMARY OF THE INVENTION

The objects mentioned above are accomplished by a metal ion-exchanged phosphorus-vanadium compound having an interlayer distance in the range of 7.0 to 8.2 Å and an ion exchange ratio of the divalent metal at least 20% obtained by treating vanadyl hydrogen orthophosphate hydrate represented by the formula (1)

$$VOHPO_4 \cdot nH_2O \tag{1}$$

wherein n fulfills the expression, $0 \leq n \leq 2.0$, with an aqueous divalent metal salt solution thereby effecting the exchange of $H^+$ present between the layers of the vanadyl hydrogen orthophosphate hydrate and drying the resultant ion exchanged compound.

The objects mentioned above are accomplished by a metal ion-exchanged phosphorus-vanadium compound having an interlayer distance in the range of 7.0 to 8.2 Å and an ion exchange ratio of the divalent metal at least 20% and obtained by treating vanadyl hydrogen orthophosphate hydrate represented by the formula (1)

$$VOHPO_4 \cdot nH_2O \tag{1}$$

wherein n fulfills the expression, $0 \leq n \leq 2.0$, with an aqueous divalent metal salt solution thereby effecting the exchange of $H^+$ present between the layers of the vanadyl hydrogen orthophosphate hydrate, drying then calcining the dried ion exchanged compound.

BRIEF DESCRIPTION OF THE DRAWINGS

FIG. 1 is a model plan view illustrating the structure of vanadyl hydrogen orthophosphate hydrate.

FIG. 2 is a model diagram illustrating a cross section of the structural diagram shown in FIG. 1.

DESCRIPTION OF THE PREFERRED EMBODIMENT

Figure 3:
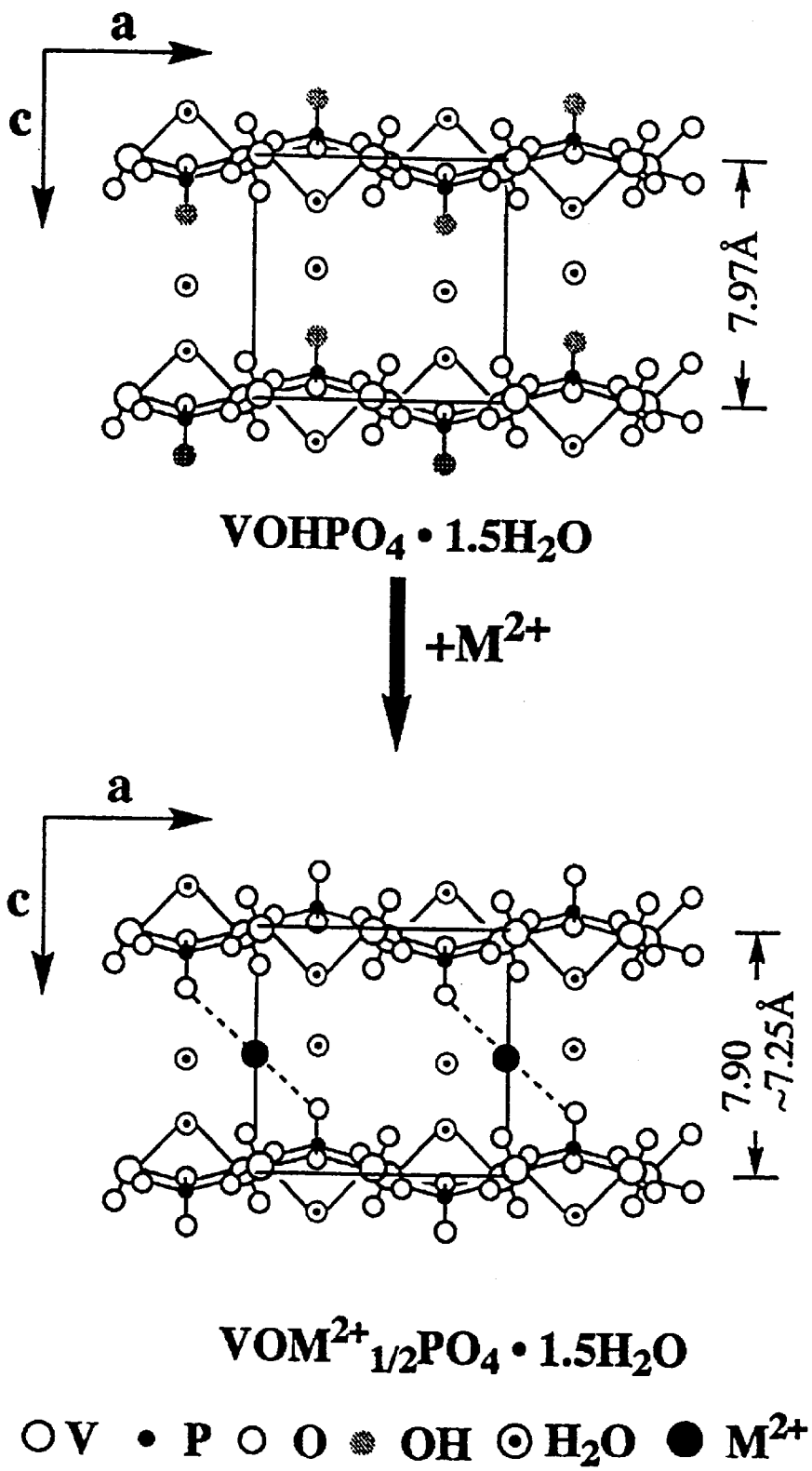
FIG. 3 is a model diagram illustrating the structure of vanadyl hydrogen orthophosphate hydrate and the cross-sectional structure of an ion exchanger thereof.

The metal ion-exchanged phosphorus-vanadium compound having an interlayer distance in the range of 7.0 to 8.2 Å in accordance with this invention is obtained by causing a vanadium compound to react with a phosphorus compound thereby forming vanadyl hydrogen orthophosphate hydrate represented by the formula (1)

$$VOHPO_4 \cdot nH_2O \tag{1}$$

wherein n fulfills the expression, $0 \leq n \leq 2.0$, preferably $1.0 \leq n \leq 2.0$, more prefeerably $1.2 \leq n \leq 1.8$, treating the vanadyl hydrogen orthophosphate hydrate with an aqueous divalent metal salt solution thereby effecting the exchange of $H^+$ present between the layers of the vanadyl hydrogen orthophosphate hydrate and drying the resultant ion exchanger. The dried ion exchanged compound, when necessary, is further calcined.

The interlayer distance of the metal ion-exchanged phosphorous-vanadium compound in accordance with the present invention is 70–8.2Å, preferably 7.1–8.1 Å, more preferably 7.2–8.0 Å.

The method for the production of the metal ion-exchanged pbosphorus vanadium compound according to this invention will be described in detail below.

For the purpose of this production, this invention permits adoption of any method which is capable of obtaining a product exhibiting a specific X-ray diffraction spectrum which will be described afterward. The typical methods available for the production are known in the following type kinds, depending on the water content of the vanadyl hydrogen orthophosphate hydrate ($VOHPO_4 \cdot nH_2O$). First, the raw materials to be used for the preparation of the catalyst will be explained.

The vanadium source may be any of the vanadium compounds which are generally adopted for the production of phosphorus-vanadium oxides. As typical examples of the vanadium compounds, pentavalent, tetravalent, or trivalent vanadium-containing compounds such as vanadium

$$VOHPO_4 \cdot nH_2O \tag{1}$$

pentoxide, metavanadates, and vanadium oxyhalides may be cited. Among other vanadium compounds mentioned above, vanadium pentoxide proves particularly advantageous.

The phosphorus source, similarly to the vanadium source, may be any of the phosphorus compounds which are generally adopted for the production of phosphorus-vanadium oxides. As typical examples of the phosphorus compounds, orthophosphoric acid, pyrophosphoric acid, phosphorous acid, polyphosphoric acid, and phosphorus pentoxide may be cited. Among other phosphorus compounds mentioned above, orthophosphoric acid proves particularly advantageous.

Method 1 for Preparation

Method 1 for preparation will be explained. The content of $H_2O$ in a compound is represented by a specific amount for the sake of convenience.

The method 1 for preparation comprises causing a vanadium compound to react with a phosphorus compound in an aqueous organic solvent thereby forming vanadyl hydrogen orthophosphate hydrate such as, for example, $VOHPO_4 \cdot 0.5H_2O$, combining the vanadyl hydrogen orthophosphate hydrate with distilled water and further with an alkali salt, then adjusting the pH value of the resultant mixture to 5–7, filtering and cleaning the mixture, and treating the cleaned mixture with an aqueous metal salt solution thereby effecting required ion exchange. Then, the resultant ion exchanger is dried and the dried ion exchanger such as, for example, $VOM_{0.5}PO_4$ is calcined when necessary. More specifically, the preparation is carried out by the following procedure.

(1) Step of Reaction of Vanadium Compound with Phosphorus Compound

This step obtains vanadyl hydrogen orthophosphate hydrate such as, for example, $VOHPO_4 \cdot 0.5H_2O$ by the reaction of a vanadium compound with a phosphorus compound in an aqueous solvent or organic solvent.

The aqueous solvent or organic solvent for the reaction of the vanadium compound with the phosphorus compound is required to combine the functions of a reducing agent for reducing the pentavalent vanadium compound and of a reaction solvent. Any of the aqueous organic solvents combining these functions can be used. As typical examples of these organic solvents, aliphatic alcohols such as isopropanol, 2-butanol, isobutanol, 2-pentanol, and isopentanol; aromatic alcohols such as benzyl alcohol, methylbenzyl alcohol, dimethylbenzyl alcohol, and ethylbenzyl alcohol; and aromatic aldehydes such as benzaldehyde, tolualdehyde, dimethyl benzaldehyde, and anisaldehyde may be cited. As the organic solvent, aqueous organic solvent is preferable. It is allowable to use aliphatic alcohols, aromatic alcohols, and aromatic aldehydes as suitably mixed. Preferably, isobutanol and benzyl alcohol are used either singly or together in a mixed state. Further, when the reaction of the vanadium compound with the phosphorous compound is carried out in the aqueous solvent, concentrated hydrochloric acid, hydrazine or hydroxylamine may be used as a reducing agent which can reduce the pentavalent vanadium to tetravalent vanadium compound.

The ratio of the amounts of the phosphorus source and the vanadium source to be used is properly in the range of 0.9/1–1.2/1, preferably 0.95/1–1.1/1 as phosphorus/vanadium (atomic ratio).

The reaction of the vanadium compound with the phosphorus compound carried out in the solvent mentioned above at a temperature in the range of 60°–150° C., preferably 80°–140° C., for a period in the range of 2–24 hours, preferably 4–12 hours produces the vanadyl hydrogen orthophosphate hydrate.

(2) Step for pH Adjustment

This step comprises combining the produced vanadyl hydrogen orthophosphate hydrate with distilled water and further with an alkali salt, then adjusting the pH value of the resultant mixture to 5–7, preferably 6–7, and filtering and cleaning the mixture.

The pH adjustment is effected generally with an alkali solution. The vanadyl hydrogen orthophosphate hydrate and distilled water added thereto are together stirred thoroughly. The resultant mixture, by gradual addition of the aqueous solution of such alkali as sodium hydroxide or potassium hydroxide, has the pH value thereof adjusted to 5–7, preferably 6–7. After the pH adjustment, the precipitate is immediately separated by filtration and thoroughly cleaned.

(3) Step for Metal Ion Exchange

This step comprises combining the washed precipitate with distilled water and subjecting the resultant mixture to a treatment with an aqueous metal salt solution to effect the ion exchange.

The resultant precipitate is added to the aqueous solution of a metal salt and then heated at a temperature in the range of 60°–100° C., preferably 80°–100° C., for a period in the range of 5–60 hours, preferably 15–60 hours, to induce an ion-exchange reaction as required. The metal salts available for this treatment include nitrates, carbonates, and organic acid salts. Preferably, divalent metal salts of such organic acids as acetic acid are used. The metal is appropriately used in an amount in the range of 0.5–5 mols per mol of the $VOHPO_4 \cdot 0.5H_2O$. As typical examples of the divalent metal, cobalt, nickel, copper, zinc, anganese, iron, magnesium, palladium, platinum, and germanium may be cited. Among other divalent metals mentioned above, cobalt, nickel, copper, and zinc prove particularly advantageous. These divalent metals may be used either singly or in the form of a mixture of two or more members. The product of the ion-exchange reaction is filtered and washed to remove the excess metal salt.

(4) Step for Drying

This step comprises drying the precipitate consequently obtained. The precipitate is dried in the stream of an inert gas or in the current of air at a temperature in the range of 150°–250° C., preferably 180°–220° C., for a period in the range of 5–14 hours, preferably 12–20 hours, to obtain an ion exchanged compound such as, for example $VOM_mPO_4$ wherein m represents a numerical value in the range of 0.1–0.5, preferably 0.15–0.5.

(5) Step for Calcination

This step comprises calcining the dried precipitate after the step for drying. This step is performed optionally.

The dried ion exchanged compound such as, for example, $VOM_{0.5}PO_4$, is pulverized or molded and then calcined in the stream of an inert gas or in the stream of a hydrocarbon gas such as butane, preferably in the stream of a mixed gas of hydrocarbon gas with air, at a temperature in the range of 350°–600° C., preferably 400°–600° C., for a period in the approximate range of 5–24 hours, preferably 10–20 hours. A concentration of hydrocarbon gas is in the range of 0.5–10% by volume, preferably 5–10% by volume calculated, as butane to total of the hydrocarbon gas and air.

Now, Method 2 for preparation will be explained. The content of the water of crystallization, $H_2O$, in a compound is represented by a specific amount for the sake of convenience. The method 2 for preparation comprises refluxing a vanadium compound and a phosphorus compound in an aqueous solvent thereby forming $VOPO_4 \cdot 2.0H_2O$, reducing the produced $\alpha\text{-}VOPO_4 \cdot 2.0H_2O$ further in an organic solvent thereby producing a vanadyl hydrogen orthophosphate hydrate such as, for example, $VOHPO_4 \cdot 1.5H_2O$, and treating this compound with an aqueous solution of a metal salt thereby inducing an ion exchange. This preparation is carried out more specifically by the following procedure.

(1) Step for Reaction of Vanadium Compound with Phosphorus Compound

This step comprises refluxing a vanadium compound and a phosphorus compound in an aqueous solvent thereby forming $VOPO_4 \cdot 2.0H_2O$.

The ratio of the amounts of the phosphorus source and the vanadium source, i.e. phosphorus/vanadium (atomic ratio), is in the range of 5/1–12/1, preferably 7/1–10/1.

The $VOPO_4 \cdot 2.0H_2O$ can be obtained by adding the vanadium source and the phosphorus source to distilled water and refluxing the resultant mixture at a temperature in the range of 60°–100° C., preferably 80°–100 °C., for a period in the range of 2–12 hours, preferably 6–10 hours.

(2) Step for Reducing $VOPO_4 \cdot 2.0H_2O$

This step comprises reducing the $\alpha\text{-}VOPO_4 \cdot 2.0H_2O$ obtained at the step mentioned above in an organic solvent thereby obtaining $VOHPO_4 \cdot 1.5H_2O$. The solvents usable for reducing $VOPO_4 \cdot 2.0H_2O$ include such 1-alkanols as 1-propanol, 1-butanol, and 1-pentanol. preferably 1-butanol. The $VOHPO_4 \cdot 1.5H_2O$ is obtained by treating $VOPO_4 \cdot 2.0H_2O$ in the solvent mentioned above at a temperature in the range of 60°–150 ° C., preferably 80°–110° C., for a period in the range of 2–24 hours, preferably 8–12 hours.

(3) Step for Metal Ion Exchange

This step comprises treating the $VOHPO_4 \cdot 1.5H_2O$ having such a structure as shown in FIG. 3 with the aqueous solution of a metal salt thereby inducing an ion-exchange reaction. The ion-exchange reaction is carried out by combining the produced $VOHPO_4 \cdot 1.5H_2O$ with the aqueous solution of a metal salt and refluxing the resultant mixture at a temperature in the range of 60°–100° C., preferably 80°–100° C., for a period in the range of 5–60 hours, preferably 15–60 hours. The metal salts available for this treatment include nitrates, sulfates, carbonates, and organic acid salts. Preferably, divalent metal salts of such organic acids as acetic acid are used. Appropriately, the metal is used in an amount in the range of 0.5–5 mols, preferably 3–5 mols per mol of the $VOHPO_4 \cdot 0.5H_2O$. As typical examples of the divalent metal, cobalt, nickelt copper, zinc, manganese, iron, magnesium, palladium, platinum, and germanium may be cited. Among other divalent metals mentioned above, cobalt, nickel, copper, and zinc prove particularly advantageous. These divalent metals may be used either singly or in the form of a mixture of two or more members. The product of the ion-exchange reaction is filtered and washed to remove the excess metal salt.

(4) Step for Drying

This step comprises drying the ion exchanged compound obtained in the form of a precipitate. The precipitate is dried in the stream of an inert gas such as nitrogen or in a stream of air at a temperature in the range of 150°–250° C., preferably 180°–220° C., for a period in the range of 5–24 hours, preferably 12–20 hours to obtain $VOM_m PO_4$. In this formula, m is a numerical value in the range of 0.1–0.5, preferably 0.15–0.5.

(5) Step for Calcination

This step comprises calcining the dried precipitate. It is carried out optionally. The dried ion exchanged compound such as, for example, $VOM_mPO_4$, is pulverized or molded and then calcined in the stream of an inert gas or in the stream of a hydrocarbon gas such as butane, preferably in the stream of a mixed gas of hydrocarbon gas with air, at a temperature in the range of 350°–600° C., preferably 400–500° C., for a period in the approximate range of 5–24 hours, preferably 10–20 hours. A concentration of hydrocarbon gas is in the range of 0.5–10% by volumes, preferably 5–10% by volume calculated as butane to total of the hydrocarbon gas and air.

By the steps mentioned above, the vanadium-phosphorus oxide of this invention is obtained.

Figure 6:
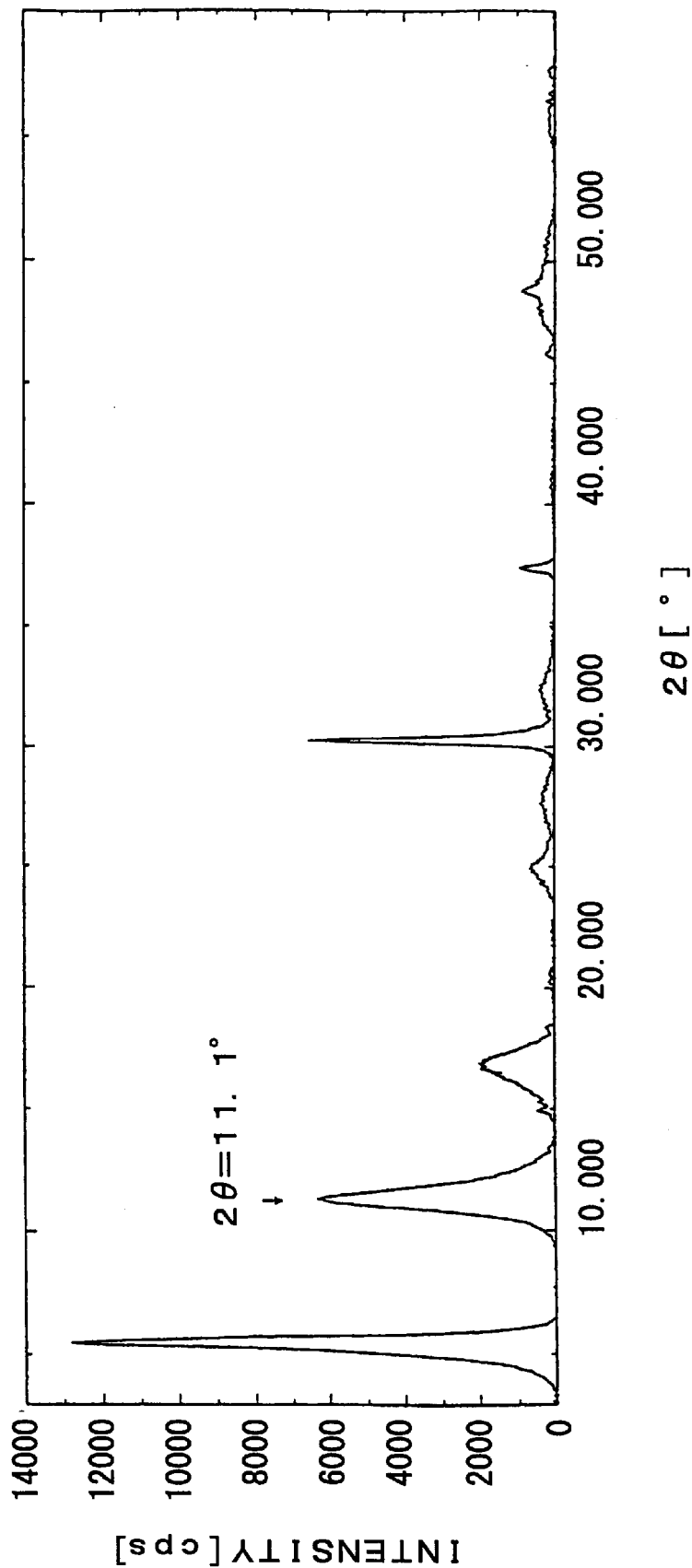
FIGS. 6 and 7 are X-ray diffraction charts illustrating one example of a metal ion-exchanged phosphorus-vanadium compound in accordance with the present invention.
Figure 7:
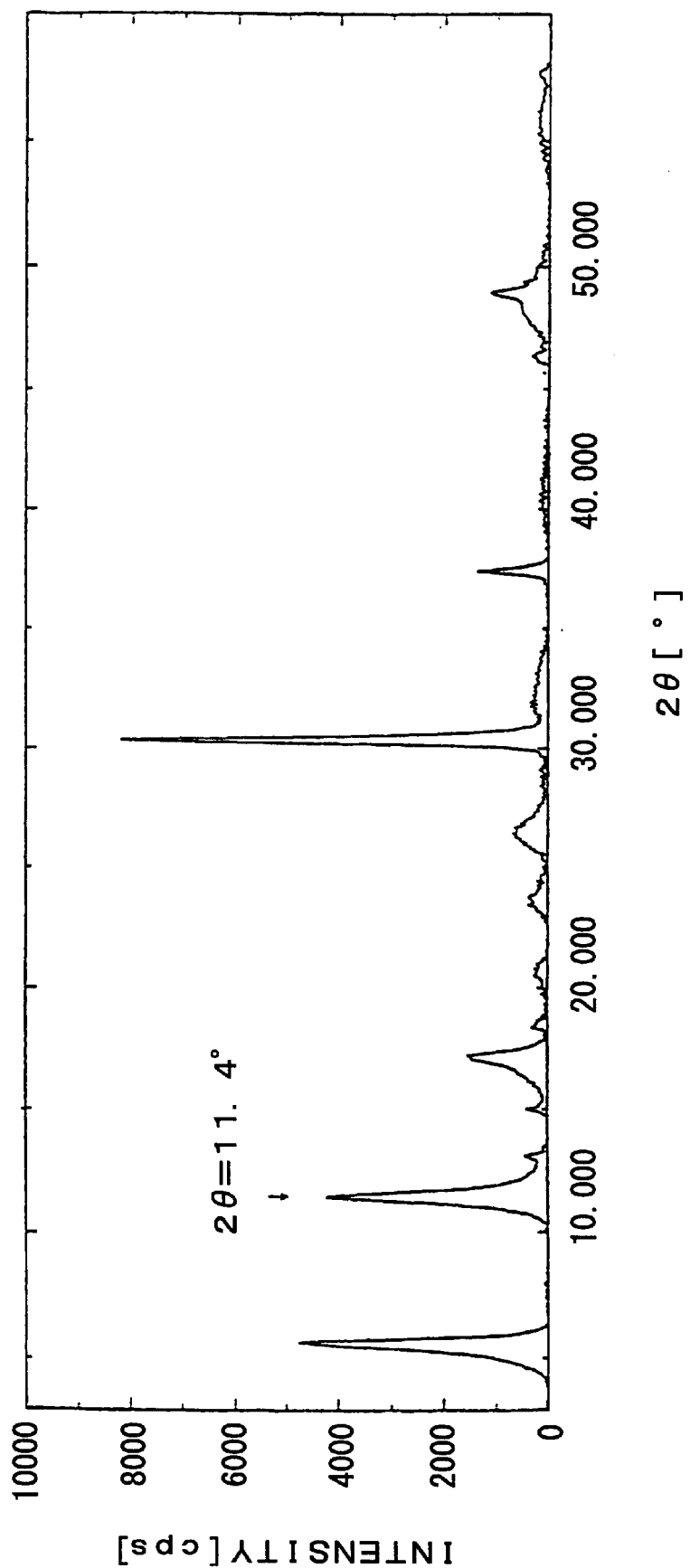
Figure 8:
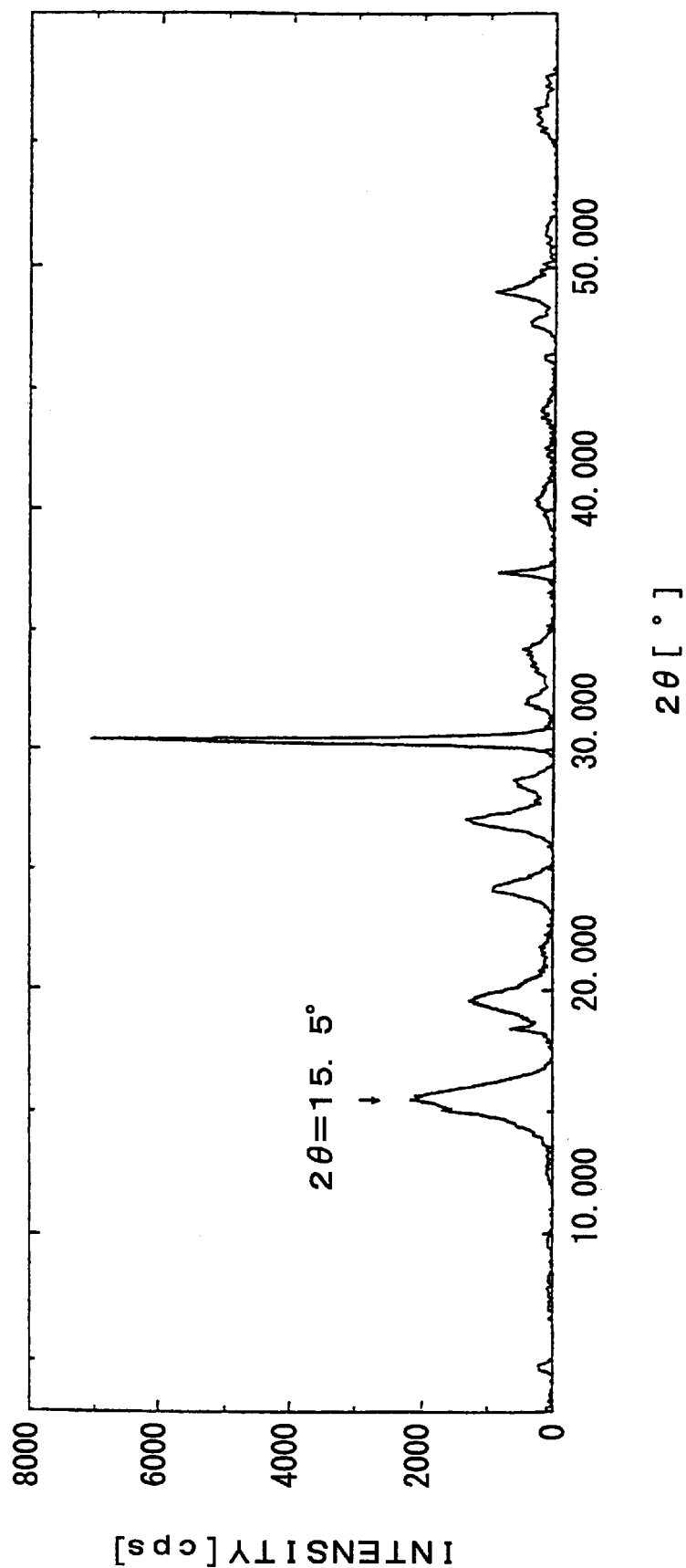
FIGS. 8 and 9 are x-ray diffraction charts illustrating one example of a metal ion-exchanged phosphorus-vanadium compound of Datta et al.
Figure 9:
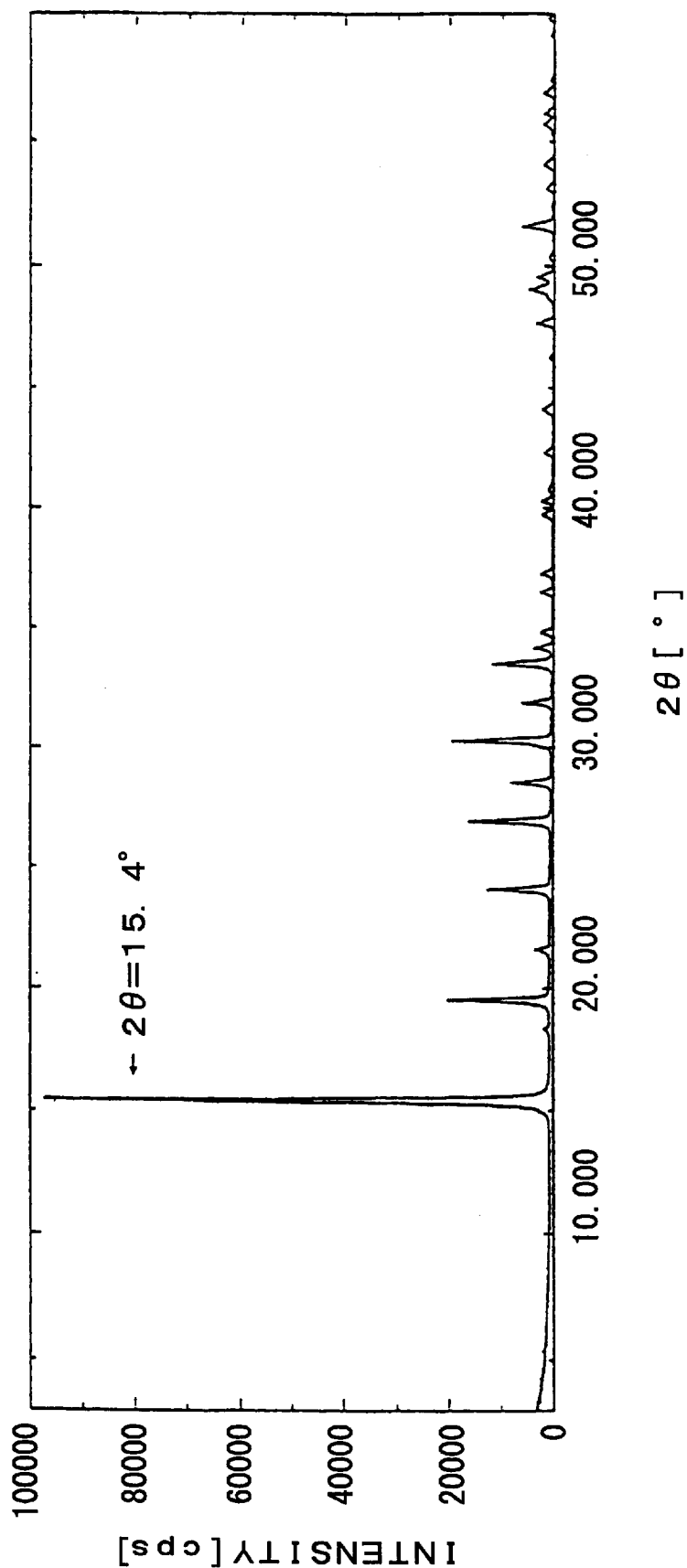

One of the features of the present invention resides in the use of the vanadyl hydrogen orthophosphate shown in FIGS. 6 and 7 as a raw matereial of the ion-exchange. Such compound is expressed by $VOHPO_4 \cdot 1.5H_2O$ as the composition, but it may be crystal water range shown in claim 1 depending on dryness state, method for preparation, et. as follows.

$VOHPO_4 \cdot nH_2O \; (0 < n \leq 2.0)$

The vanadyl hydrogen orthophosphate which is raw material of the present invention has the following X-ray diffraction peaks (d values one shown in Table 1 of the specification).

d values (Å)=7.97, 2.94 and 2.41

(2θ=11.1°, 30.4° and 37.3°).

We have determined an amount of the divalent metal ion in the divalent metal ion-exchanged phosphorus-vanadium compound shown in Examples of the present invention and calculated ion-exchange ratioes.

The divalent metal ion-exchanged phosphorus-vanadium compound of the present invention is a compound obtained by ion-exchanging protons between interlayers of vanadyl hydrogen orthophosphate having crystal structure shown in FIGS. 6 and 7 with the divalent metal ions and is expressed by the following formula:

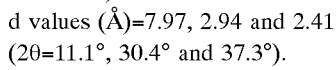
$VOHPO_4 \cdot nH_2O + M^{2+} \rightarrow VO(M^{2+})_m PO_4 \cdot nH_2O (0.1 \leq m \leq 0.5)$ Therefore, when m of the divalent metal ion is 0.5, an ion-exchange ratio assumed 100%, and the ion-exchange ration is calculated by the following formula;

Ion-exchange ratio(%)=(m/0.5)×100

The ion-exchange ratios calculated by the above mentioned formula are shown in Table 4.

Thus an ion-exchange ratio of the divalent metal is not less than 20%, preferably not less than 30%.

When the metal ion-exchanged phosphorus-vanadium compound obtained by the method 1 for preparation or the method 2 for preparation mentioned above is used as a catalyst, the compound can be used as molded in a specific form. The molding can be carried out in the presence of a molding aid. As typical examples of the molding aid to be effectively used herein, inorganic substances such as silica gel, alumina sol, and talc and organic substances such as graphite and fatty acid salts may be cited. Further, the molding may be carried out in the presence of fibers of an inorganic substance. The catalyst of this invention for gas phase oxidation can be used either singly or can be used as molded together with such a carrier as silica, alumina, titania, silicon carbide, or ceramic substance or deposited on such a carrier. It has no particular limit to impose as to shape. It can be molded in the form of powder, spheres, cylinders, arcs, or saddles by such known methods as tableting or extrusion molding.

As typical examples of the catalytic gasphase oxidation reaction, the reactions for the production of maleic anhydride by the oxidation of butane, the production of methacrolein and methacrylic acid by the oxidation of isobutane, the production of methacrylic acid by the oxidation of methacrolein, the production of acrylonitrile by the ammoxidation of propane, and the production of methacrylic acid by the oxydehydroqenation of isobutyric acid may be cited. The catalyst can be particularly used for the selective oxidation of normal butane into maleic anhydride in the presence of molecular oxygen.

Now, this invention will be described more specifically below with reference to working examples.

EXAMPLE 1

In 100 ml of distilled water, 6.0 g of $VOHPO_4.0.5H_2O$ which was prepared by the reaction of vanadium pentoxide ($V_2O_5$) in isobutanol with 99% orthophosphoric acid at 80° C. was stirred. The resultant mixture was adjusted to pH 6.5 by gradual addition of an aqueous 1.0 mol/liter sodium hydroxide solution. The mixture was immediately filtered and repeatedly washed to remove excess sodium ions. This precipitate and 250 ml of an aqueous 0.2 mol/liter divalent cobalt acetate solution were together refluxed at 80° C. for 48 hours. The refluxed mixture was filtered and washed to remove excess metal ions. The cleaned mixture was dried overnight at room temperature and further dried in a stream of argon at 200° C. for 3 hours. The dried mixture was confirmed to be a divalent cobalt ion exchanged compound of $VOM_{0.5}PO_4$. The cobalt ion exchanged compound thus obtained was calcined in the stream of air-mixed gas having a normal butane concentration of 2.0 vol % at 480° C. for 12 hours.

Figure 4:
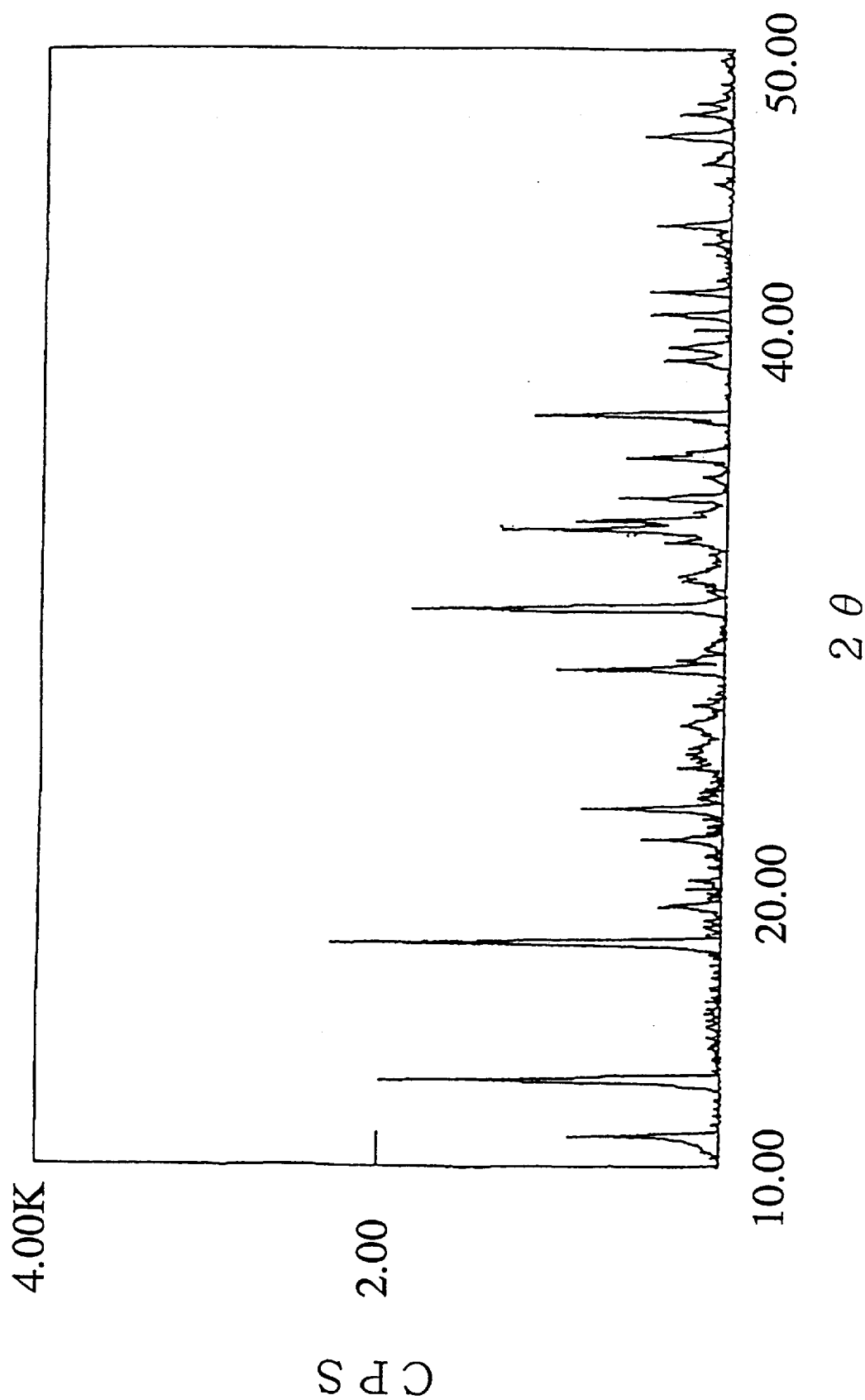
FIG. 4 is an X-ray diffraction chart illustrating one example of a metal ion-exchanged phosphorus-vanadium compound according to this invention.

The X-ray diffraction spectrum of a dry mass of the produced cobalt ion-exchanged phosphorus-vanadium oxide ($VOCO_{0.5}PO_4$) was found to have such main peaks as shown in Table 1. The X-ray diffraction spectrum of $VOHPO_4.1.5H_2O$ was also shown in Table 1 for reference. Further, lattice constants of $VOHPO_4.1.5H_2O$ and the cobalt ion-exchanged phosphorous-vanadium oxide are shown in Table 2. The X-ray diffraction chart of this compound was as shown in FIG. 4.

The X-ray diffraction spectrum of a sintered mass of the cobalt-exchanged phosphorus-vanadium oxide ($VOCo_{0.5}PO_4$) was found to have such main peaks as shown in Table 3.

EXAMPLE 2

$VOHPO_4.1.5H_2O$ was prepared by refluxing vanadium pentoxide ($V_2O_5$) and 85% orthophosphoric acid in distilled water to form $VOPO_4.2.0H_2O$ and ref luxing the produced compound in 1-butanol at 110° C. In 250 ml of an aqueous 0.2 mol/liter divalent cobalt acetate solution, 6.0 g of the ($VOHPO_4.1.5H_2O$) was refluxed at 80° C. for 48 hours. The mixture resulting from the reflux was filtered and washed to remove excess metal ions. The cleaned mixture was dried overnight at room temperature. It was further dried in a stream of argon at 200° C. for 3 hours. This dried mixture was found to be a divalent cobalt ion exchanged compound of ($VOM_{0.5}PO_4$). The cobalt ion exchanged compound was calcined in a stream of air-mixed gas having a normal butane concentration of 2.0 vol % at 480° C. for 12 hours.

Figure 5:
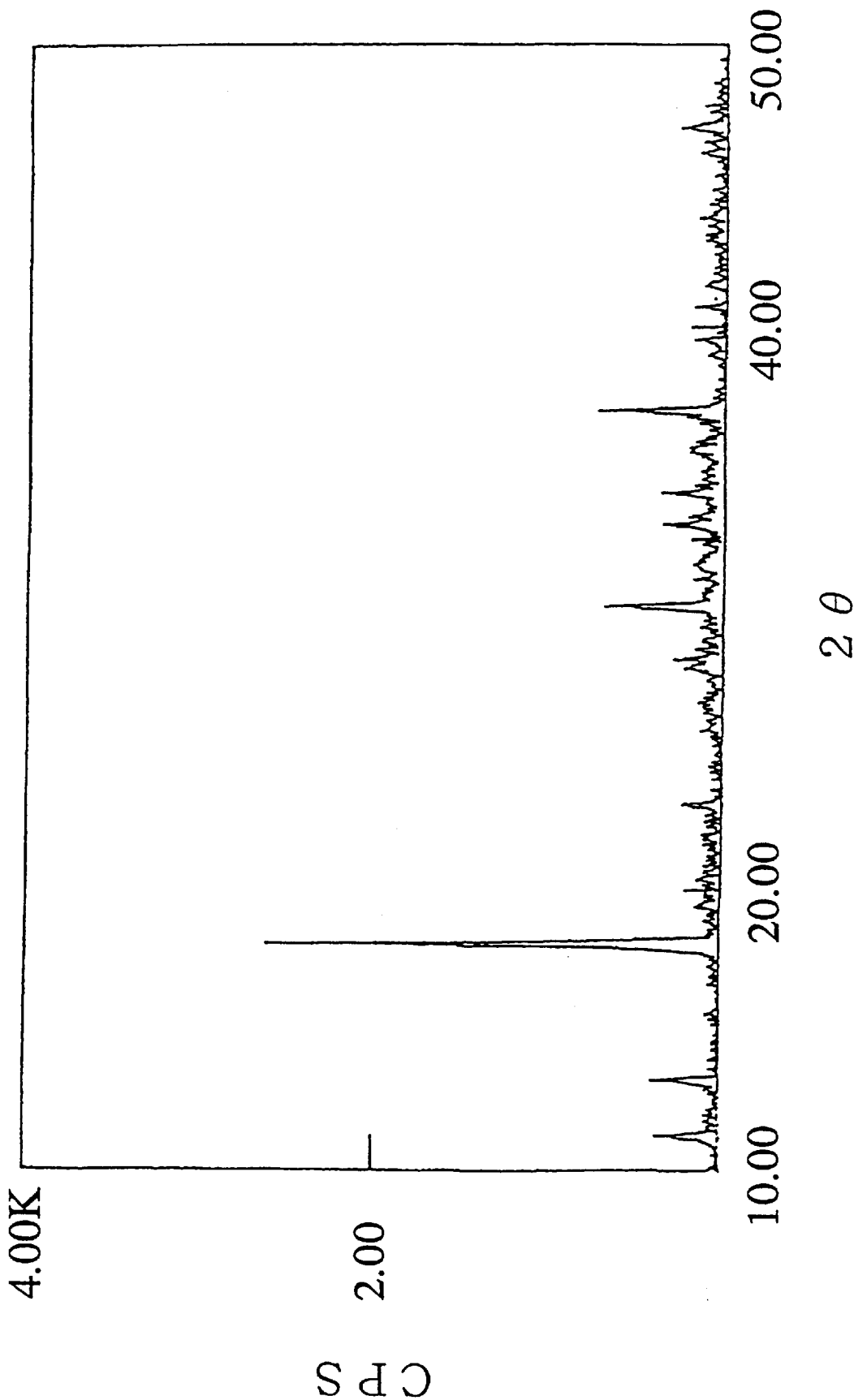
FIG. 5 is an X-ray diffraction chart illustrating another example of the metal ion-exchanged phosphorus-vanadium compound according to this invention.

The X-ray diffraction spectrum of a dried mass of the produced cobalt ion-exchanged phosphorus-vanadium oxide ($VOCo_{0.5}PO_4$) was found to have such main peaks as shown in Table 1. The X-ray diffraction chart of this compound was as shown in FIG. 5.

The X-ray diffraction spectrum of a sintered mass of the produced cobalt-exchanged phosphorus-vanadium oxide ($VOCo_{0.6}PO_4$) was found to have such main peaks as shown in Table 3.

EXAMPLE 3

In 100 ml of distilled water, 6.0 g of $VOHPO_4.0.5H_2O$ which was prepared by the reaction of vanadium pentoxide ($V_2O_5$) in 2-butanol with 99% orthophosphoric acid at 80° C. was stirred. The resultant mixture was adjusted to pH 6.5 by gradual addition of an aqueous 1.0 mol/liter sodium hydroxide solution. The mixture was immediately filtered and repeatedly washed to remove excess sodium ions. This precipitate and 250 ml of an aqueous 0.2 mol/liter divalent nickel acetate solution were together refluxed at 90° C. for 55 hours. The refluxed mixture was filtered and washed to remove excess metal ions. The cleaned mixture was dried overnight at room temperature and further dried in a stream of argon at 200° C. for 3 hours. The dried mixture was confirmed to be a divalent nickel ion exchanged compound of $VOM_{0.5}PO_4$. The nickel ion exchanged compound thus obtained was calcined in the steam of air-mixed gas having a normal butane concentration of 2.0 vol % at 460° C. for 12 hours.

The X-ray diffraction spectrum of a dry mass of the produced nickel ion-exchanged phosphorus-vanadium oxide ($VONi_{0.5}PO_4$) was found to have such main peaks as shown in Table 1. Lattice constant of the nickel ion exchanged phosphorous-vanadium oxide is shown in Table 2.

The X-ray diffraction spectrum of a sintered mass of the nickel-exchanged phosphorus-vanadium oxide ($VONi_{0.5}PO_4$) was found to have such main peaks as shown in Table 3.

EXAMPLE 4

$VOHPO_4.1.5H_2O$ was prepared by refluxing vanadium pentoxide ($V_2O_5$) and 85% orthophosphoric acid in distilled water to form $VOPO_4.2.0H_2O$ and refluxing the produced compound in 1-butanol at 110° C. In 250 ml of an aqueous 0.2 mol/liter divalent nickel acetate solution, 6.0 g of the ($VOHPO_4.1.5H_2O$) was refluxed at 85° C. for 60 hours. The mixture resulting from the reflux was filtered and washed to remove excess metal ions. The cleaned mixture was dried overnight at room temperature. It was further dried in a stream of argon at 200° C. for 3 hours. This dried mixture was found to be a divalent nickel ion exchanged compound of ($VOM_{0.5}PO_4$). The nickel ion exchanged compound was calcined in a stream of air-mixed gas having a normal butane concentration of 2.0 vol % at 480° C. for 12 hours.

The X-ray diffraction spectrum of a dried mass of the produced nickel-exchanged phosphorus-vanadium oxide ($VOCo_{0.5}PO_4$) was found to have such main peaks as shown in Table 1.

The X-ray diffraction spectrum of a sintered mass of the produced nickel-exchanged phosphorus-vanadium oxide (VOCo$_{0.6}$PO$_4$) was found to have such main peaks as shown in Table 3.

The X-ray diffraction spectrum of a dried mass of the produced zinc-exchanged phosphorus-vanadium oxide (VOZn$_{0.4}$PO$_4$) was found to have such main peaks as shown in Table 1. Lattice constant of the zinc ion-exchanged phosphorus oxide is shown in Table 2.

TABLE 1

| | VOHPO$_4$·1.5H$_2$O | | Ni | | Co | | Cu | | Zn | |
|---|---|---|---|---|---|---|---|---|---|---|
| hkl | d value (Å) | strength | d value (Å) | strength | d value (Å) | strength | d value (Å) | strength | d value (Å) | strength |
| 001 | 7.97 | S | 7.9 | W | 7.85 | W | 7.31 | VS | 7.25 | VS |
|  |  |  | 6.71 | W | 6.64 | W—M |  |  | 6.56 | W |
| 020 | 4.81 | W | 4.87 | W | 4.89 | VS | 4.85 | S | 4.6 | W |
|  |  |  | 3.81 | W | 3.85 | W | 3.77 | M |  | W |
| 112 | 3.30 | W | 3.3 | W | 3.2 | W |  |  |  | W |
| 220 | 2.94 | VS | 2.94 | W | 2.98 | W | 2.93 | S | 2.98 | W |
| 202 | 2.72 | W | 2.7 | W | 2.71 | W |  |  |  | W |
|  |  |  | 2.61 | W | 2.62 | W | 2.64 | S | 2.63 | W |
| 040 | 2.41 | W | 2.39 | W | 2.42 | M | 2.43 | W | 2.47 | W |

EXAMPLE 5

In 100 ml of distilled water, 6.0 got VOHPO$_4$·0.5H$_2$O which was prepared by the reaction of vanadium pentoxide (V$_2$O$_5$) in 2-butanol with 99% orthophosphoric acid at 80° C. was stirred. The resultant mixture was adjusted to pH 6.5 by gradual addition of an aqueous 1.0 mol/liter sodium hydroxide solution. The mixture was immediately filtered and repeatedly washed to remove excess sodium ions. This precipitate and 250 ml of an aqueous 0.2 mol/liter divalent copper acetate solution were together refluxed at 90° C. for 55 hours. The refluxed mixture was filtered and washed to remove excess metal ions. The cleaned mixture was dried overnight at room temperature and further dried in a stream of argon at 200° C. for 3 hours. The dried mixture was confirmed to be a divalent copper ion exchanged compound of VOM$_{0.5}$PO$_4$. The copper ion exchanged compound thus obtained was calcined in the steam of air-mixed gas having a normal butane concentration of 2.0 vol % at 480° C. for 12 hours.

The X-ray diffraction spectrum of a dry mass of the produced copper ion-exchanged phosphorus-vanadium oxide (VONi$_{0.5}$PO$_4$) was found to have such main peaks as shown in Table 1. Lattice constant of the copper ion-exchanged phosphorous-vanadium oxide is shown in Table 2.

EXAMPLE 6

VOHPO$_4$·1.5H$_2$O was prepared by refluxing vanadium pentoxide (V$_2$O$_5$) and 85% orthophosphoric acid in distilled water to form VOPO4·2.0H$_2$O and refluxing the produced compound in 1-butanol at 110° C. In 250 ml of an aqueous 0.2 mol/liter divalent zinc acetate solution, 6.0 g of the (VOHPO$_4$·1.5H$_2$O) was refluxed at 80° C. for 30 hours. The mixture resulting from the reflux was filtered and washed to remove excess metal ions. The cleaned mixture was dried overnight at room temperature. It was further dried in a stream of argon at 200° C. for 3 hours. This dried mixture was found to be a divalent zinc ion exchanged compound of (VOM$_{0.4}$PO$_4$). The zinc ion exchanged compound was calcined in a stream of air-mixed gas having a normal butane concentration of 2.0 vol % at 480° C. for 12 hours.

TABLE 2

| Lattice Const. (Å) | a | b | c |
|---|---|---|---|
| VOHPO$_4$·1.5H$_2$O | 7.43 | 9.62 | 7.97 |
| VONi$_{0.5}$PO$_4$·1.5H$_2$O | 7.43 | 9.74 | 7.90 |
| VOCo$_{0.5}$PO$_4$·1.5H$_2$O | 7.43 | 9.78 | 7.84 |
| VOCu$_{0.5}$PO$_4$·1.5H$_2$O | 7.43 | 9.70 | 7.31 |
| VOZn$_{0.5}$PO$_4$·1.5H$_2$O | 7.43 | 9.88 | 7.25 |

A factor showing the interlayer distance of the phousphorous-vanadium compound is hkl=1 in Table 1 and the value of c axis about the lattice constant.

TABLE 3

| | Ni | | Co | |
|---|---|---|---|---|
| | d value (Å) | Strength | d value (Å) | Strength |
| | 5.86 | W | 5.79 | W |
| | 4.46 | W | 4.43 | W-M |
| | 3.45 | W | 3.4 | W-M |
| | 3.07 | S | 3.04 | VS |
| | 2.95 | W | 2.89 | W-M |
| | 2.57 | VS | 2.55 | W-M |
| | 2.14 | W | 2.12 | W |

EXAMPLE 7

In 100 ml of distilled water, 6.00g of VOHPO$_4$·0.5H$_2$O which was prepared by the reaction of vanadium pentoxide (V$_2$O$_5$) in isobutanol with 99% orthophosphoric acid at 80*° C. was stirred. The resultant mixture was adjusted to pH 6.5 by gradual 15 addition of an aqueous 1.0 mol/liter sodium hydroxide solution. The mixture was immediately filtered and repeatedly washed to remove excess sodium ions. It was dried at 120° C. for 12 hours.

Crystal water in the compound thus obtained was calculated to VOHPO$_4$·1.58H$_2$O from weight decrease determined using a differential thermal analysis method.

The X-ray diffraction spectrum of vanadyl hydrogen torthophosphate (VOHPO$_4$·1.5H$_2$O) thus obtained is shown in FIG. A. Characteristic peak of 2θ=11.1°(d=7.9 Å) of this compound was observed in the XRD pattern, so it shows that the interlayer distance of the compound is 7.0 to 8.2 Å.

EXAMPLE 8

VOHPO$_4$·1.5H$_2$O was perpared by refluxing vanadium pentoxide (V$_2$O$_5$) and 85% orthophosphoric acid in distilled water to form vanadyl hydrogen orthophosphate (VOPO$_4$·2.0H$_2$O) and refluxing the produced compound in 1-butanol at 110° C. to obtain vanadyl hydrogen orthophosphate (VOHPO$_4$·1.5H$_2$O). The precipitate thus obtained was filtered and dried at 120° C. for 12 hours.

Crystal water in the compound thus obtained was calculated to VOHPO$_4$·1.42H$_2$O from weight decrease determined using a differential thermal analysis method.

The X-ray diffraction spectrum of vanadyl hydrogen orthophosphate (VOHPO$_4$·1.5H$_2$O) thus obtained is shown in FIG. B. Characteristic peak of 2θ=11.4°(d=7.8 Å) of this compound was observed in the XRD pattern, so it shows that the interlayer distance of the compound is 7.0 to 8.2 Å.

EXAMPLE 9

45.5 g of vanadium pentoxide (V$_2$O$_5$) ws suspended in a mixed solvent of 350 ml of isobutanol and 100 of benzyl alcohol and reduced for 5 hours under maintaining a emperature of 110° C. 49.5 g of 99% orthophosphoric acid dissolved in 100 ml of isobutanol was added into a reduced vanadium solution. The solution was stirred for 10 hours under maintaining a temperature of 110° C. to obtain blue precipitate. After cooling the resultant reaction slurry, the precipitate thus obtained was filtered, washed with acetone and the precipitate thus obtained was dried at 120° C. for 12 hours.

Crystal water in the compound thus obtained was calculated to VOHPO$_4$·0.57H$_2$O from weight decrease determined using a differential thermal analysis method.

The X-ray diffraction spectrum of vanadyl hydrogen orthophosphate (VOHPO$_4$·0.5H$_2$O) thus obtained is shown in FIG. C. It is clear from the XRD pattern that the compound thus obtained is the same as vanadyl hydrogen orthophosphate described in Datta et al (it corresponds to FIG. 1-1 in Datta et al). Characteristic peak of 2θθ=15.5° (d=5.7 Å) of this compound was observed in the XRD pattern, so it shows that the interlayer distance of the compound is 5.6 to 5.8 Å.

The peaks at 2θ=11.1° to 11.4° observed in the XRD patterns of Experiments I and II cannot be observed.

EXAMPLE 10

55.1 g of 85% orthophosphoric acid and 40 g of hydroxylamine hydrochloride (NH$_2$OH.HCl) were dissolved into 350 ml of distilled water and the solution thus obtained was stirred under heating at 60° C. 45.5 g of vanadium pentoxide was gradually added into the solution under avoiding foaming. After addition, the solution was heated at 80° C. and maintained the temperature under stirring and concentrated to about 150 ml. The concentrated slurry was further dried at 120° C. to evaporate dryness. In order to remove chloride ion in the blue dried product thus obtained, it was added into 200 ml of boiled water under stirring, filtered and washed with distilled water. Removal operation of chloride ion was repeated for three times. The light blue compound thus obtained was dried at 120° C. for 12 hours.

Crystal water in the compound thus obtained was calculated to VOHPO$_4$·0.47H$_2$O from weight decrease determined using a differential thermal analysis method.

The X-ray diffraction spectrum of vanadyl hydrogen orthophosphate (VOHPO$_4$·0.5H$_2$O) thus obtained is shown in FIG. D. It is clear from the XRD pattern that the compound thus obtained is the same as vanadyl hydrogen orthophosphate described in Datta et al (it corresponds to FIG. 1-2 in Datta et al). Characteristic peak of 2θ=15.4° (d=5.7 Å) of this compound was observed in the XRD pattern, so it shows that the interlayer distance of the compound is 5.6 to 5.8 Å.

The peaks at 2θ=11.1° to 11.4° observed in the XRD patterns of Experiments I and II cannot be observed.

EXAMPLES 11–16

Ion-exchange ratioes of the divalent metal ion-exchanged phosphorus-vanadium compounds described in Examples 1 to 6 were determined by a fluorescent X-ray analysis method.

The divalent metal ion-exchanged phosphorus-vanadium compound of the Hashiba et al is a compound obtained by ion-exchanging protons between interlayers of vanadyl hydrogen orthophosphate having crystal structure shown in FIG. 6 or 7 with the divalent metal ions and is expressed by the following formula:

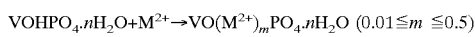

VOHPO$_4$·$n$H$_2$O+M$^{2+}$→VO(M$^{2+}$)$_m$PO$_4$·$n$H$_2$O (0.01≦m ≦0.5)

Therefore, when m of the divalent metal ion is 0.5, an ion-exchange ratio assumed 100%, and the ion-exchange ration is calculated by the following formula:

Ion-exchange ratio(%)=($m$/0.5)×100

The ion-exchange ratios calculated by the above mentioned formula are shown in Table 6.

according to Datta et al, there is described that a palladium content in the aqueous medium method is 0.61%, so the chemical composition of the compound is as follows:

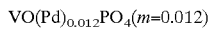

VO(Pd)$_{0.012}$PO$_4$($m$=0.012)

Thus the ion-exchange ratio is 2.4%. Therefore, the ion-exchange ratio of the phosphorus-vanadium compound of Datta et al is extremely lower than those of the present invention. However, Datta et al does not disclose how to determine the amount of palladium content, so 0.61% of the palladium content in the compound cannot exactly understand the base of the content.

TABLE 4

Ion-exchange ratio of divalent metal ion-exchanged phosphorus-vanadium compound

| Example | Divalent metal ion (m) | Ion-exchange ratio (%) |
|---|---|---|
| 11 | Co = 0.489 | 97.8 |
| 12 | Co = 0.512 | 102.4 |
| 13 | Ni = 0.491 | 98.2 |
| 14 | Ni = 0.479 | 95.8 |
| 15 | Cu = 0.189 | 37.8 |
| 16 | Zn = 0.321 | 64.2 |

EXAMPLES 17-20

Synthesis of Maleic Anhydride by Oxidation of n-butane

The terms "conversion," "selectivity," and "yield" are defined as follows.

Conversion (mol %)=(Number of mols of butane consumed by reaction/number of mols of butane fed to the reaction)×100

Selectivity (mol %)=(Number of mols of formed maleic anhydride/number of mols of butane consumed by reaction)×100

Yield (mol %)=(Conversion Selectivity)×100

A sample, 10 g in weight, of each metal ion-exchanged vanadium-phosphorus oxides obtained in Example 1 and Examples 4–6 was molded in the form of pellets, 5 mm in diameter and 5 mm in height. A flow type reaction vessel was packed with the pellets. A mixed gas comprising n-butane with air having a n-butane concentration of 1.5 vol % was introduced at a spatial velocity of 2000 hr$^{-1}$ into the reaction vessel to induce gasphase oxidation of n-butane. The results are shown in Table 5.

TABLE 5

| Example | Catalyst | Reaction temperature (° C.) | Conversion (%) | Selectivity (%) |
|---|---|---|---|---|
| Example 17 | Catalyst of Ex. 1 (Co) | 450 | 75 | 58 |
| Example 18 | Catalyst of Ex. 4 (Ni) | 450 | 80 | 52 |
| Example 19 | Catalyst of Ex. 5 (Cu) | 450 | 85 | 49 |
| Example 20 | Catalyst of Ex. 6 (Zn) | 450 | 80 | 57 |

EXAMPLES 21–24

Synthesis of methacrolein and methacrylic acid by oxidation of 1-butane

The terms "conversion," "selectivity," and "yield" are defined as follows.

Conversion (mol %)=(Number of mols of butane consumed by reaction/number of mols of butane fed to the reaction)×100

Selectivity of methacrolein (mol %)=(Number of mols of formed methacrolein/number of mols of butane consumed by reaction)×100

Selectivity of methacrylic acid (moll)=(Number of mols of formed methacrylic acid/number of mols of butane consumed by reaction)×100

Yield (mol %)=(Conversion x Selectivity)×100

A sample, 10 g in weight, of each metal ion-exchanged vanadium-phosphorus oxides obtained in Example 1 and Examples 4–6 was molded in the form of pellets, 5 mm in diameter and 5 mm in height. A flow type reaction vessel was packed with the pellets. A mixed gas comprising l-butane and steam with air having a 1-butane concentration of 20 volt and a steam concentration of 10 volt was introduced at a spatial velocity of 2000 hr$^{-1}$ into the reaction vessel to induce gaseous-phase oxidation of n-butane. The results are shown in Table 6.

TABLE 6

| Example | Catalyst | Reaction temperature (° C.) | Conversion (%) | Selectivity (%) | |
|---|---|---|---|---|---|
| | | | | Metha-crolein | Metha-acrylic acid |
| Example 21 | Catalyst of Ex. 1 (Co) | 450 | 15 | 11 | 3.5 |
| Example 22 | Catalyst of Ex. 4 (Ni) | 450 | 10 | 14 | 2.5 |
| Example 23 | Catalyst of Ex. 5 (Cu) | 450 | 17 | 19 | 4.0 |
| Example 24 | Catalyst of Ex. 6 (Zn) | 450 | 19 | 10 | 1.5 |

The entire disclose of Japanese Patent Application Nos. 8-52001 and 8-52002 both filed on Mar. 8, 1996 including specification, claims, drawing and summary are incorporated herein by reference in its entirety.

What is claimed is:

1. A divalent metal ion-exchanged orthorhombic phosphorus-vanadium compound wherein axis "a" is not equal to axis "b" having an interlayer distance in the range of 7.1 to 8.1 Å and an ion exchange ratio of the divalent metal of at least 20% obtained by treating a vanadyl hydrogen orthophosphate hydrate represented by the formula (1)

VOHPO$_4$nH$_2$O wherein n fulfills the expression, $0 \leq n \leq 2.0$, with an aqueous divalent metal salt solution thereby effecting the exchange of H present between the layers of said vanadyl hydrogen orthophosphate hydrate and drying the resultant ion exchanged compound.

2. A compound according to claim 1, wherein said divalent metal is at least one member selected from the group consisting of cobalt, nickel, copper, zinc, manganese, iron, magnesium, palladium, and germanium.

3. A compound according to claim 1 wherein said drying is carried out at a temperature in the range of 150° to 250° C.

4. A solid catalyst comprising a metal ion-exchanged phosphorus-vanadium compound set forth in claim 1.

5. A catalyst for the gas phase partial oxidation of a hydrocarbon, comprising a metal ion-exchanged phosphorus-vanadium compound set forth in claim 1.

6. A divalent metal ion-exchanged orthorhombic phosphorus-vanadium compound wherein axis "a" is not equal to axis "b" having an interlayer distance in the range of 7.1 to 8.1 Å and an ion exchange ratio of the divalent metal of at least 20% obtained by treating a vanadyl hydrogen orthophosphate hydrate represented by the formula VOHPO$_4$nH$_2$O wherein n fulfills the expression, $0 < n < 2.0$, with an aqueous divalent metal salt solution thereby effecting the exchange of H present between the layers of said vanadyl hydrogen orthophosphate hydrate, drying, then calcining the dried ion exchanged compound.

7. A compound according to claim 6, wherein said calcination is carried out in the presence of a hydrocarbon under an reducing atmosphere at a temperature in the range of 350° to 600° C.

8. A compound according to claim 6, wherein said divalent metal is at least one member selected from the group consisting of cobalt, nickel, copper, zinc, manganese, iron, magnesium, palladium, and germanium.

9. A compound according to claim 6, wherein said drying is carried out at a temperature in the range of 150° to 250° C.

10. A solid catalyst comprising a metal ion-exchanged phosphorus-vanadium compound set forth in claim 6.

11. A catalyst for the gas phase partial oxidation of a hydrocarbon, comprising a metal ion-exchanged phosphorus-vanadium compound set forth in claim 6.

12. A method for production of a divalent metal ion-exchanged orthorhombic phosphorus-vanadium compound wherein axis "a" is not egual to axis "b" having an interlayer distance in the range of 7.1 to 8.1 Å which comprises adjusting the pH of an aqueous vanadyl hydrogen orthophosphate solution to 5–7, adding an aqueous divalent metal salt solution thereto so as to effect the exchange of H$^+$ present between the layers of said vanadyl hydrogen orthophosphate and drying the resultant ion exchanged compound.

13. A method according to claim 12, wherein the drying is carried out at a temperature of 150° to 250° C.

14. A method according to claim 12, wherein said adjustment of pH is carried out by adding an alkali salt.

15. A method according to claim 12, wherein said resultant exchanged compound is further calcined.

16. A method according to claim 15, wherein the calcination is carried out at a temperature of 350° to 600° C.

17. A method for production of a divalent metal ion-exchanged orthorhombic phosphorus-vanadium compound wherein axis "a" is not equal to axis "b" having an interlayer distance in the range of 7.1 to 8.1 Å which comprises refluxing a vanadium compound and a phosphorus compound in an aqueous solvent thereby forming a phosphovanadium oxide, reducing said oxide in an organic reducing solvent to obtain a vanadyl hydrogen orthophosphate, drying the vanadyl hydrogen orthophosphate and adding the dried product to an aqueous divalent metal solution so as to form said metal ion-exchanged phosphorus-vanadium compound.

18. A method according to claim 17, wherein the drying is carried out at a temperature of 150° to 250° C.

19. A method according to claim 17, wherein said metal ion-exchanged phosphorus-vanadium compound is further calcined.

20. A method according to claim 19, wherein the calcination is carried out at a temperature of 350° to 600° C.

21. A method according to claim 17, wherein a phosphorus/vanadium (atomic ratio) is 5/1 to 12/1.

22. A method according to claim 17, wherein said organic reducing solvent is an 1-alkanol.

23. A method according to claim 17, wherein said reduction is carried out at a temperature of 60° to 150° C.

* * * * *